United States Patent [19]
Motomura et al.

[11] Patent Number: 5,667,684
[45] Date of Patent: Sep. 16, 1997

[54] MATERIAL FOR REMOVING HIV AND ITS RELATED SUBSTANCES

[75] Inventors: Tadahiro Motomura; Yuko Miyashita; Takashi Ohwada; Makoto Onishi, all of Kanagawa; Naoki Yamamoto, Tokyo, all of Japan

[73] Assignee: Terumo Kabushiki Kaisha, Tokyo, Japan

[21] Appl. No.: 429,101

[22] Filed: Apr. 26, 1995

[30] Foreign Application Priority Data

Apr. 28, 1994 [JP] Japan ..................... 6-091793

[51] Int. Cl.⁶ ..................... B01D 71/26; B01D 71/34; B01D 71/78; B01D 71/82
[52] U.S. Cl. ............ 210/506; 210/500.21; 210/500.24; 210/500.36; 210/500.42; 210/504; 502/401; 502/402
[58] Field of Search .............. 210/490, 500.21, 210/500.24, 500.36, 500.42, 506, 504; 502/401, 402

[56] References Cited

U.S. PATENT DOCUMENTS

| | | |
|---|---|---|
| 4,138,287 | 2/1979 | Andersson et al. . |
| 4,200,726 | 4/1980 | Ishii et al. ............ 210/500.33 |
| 4,576,927 | 3/1986 | Kuroda et al. ............ 502/402 |
| 5,041,079 | 8/1991 | Takashima et al. ............ 604/5 |
| 5,064,866 | 11/1991 | Toyomoto et al. ............ 521/27 |
| 5,071,880 | 12/1991 | Sugo et al. ............ 210/490 |
| 5,407,581 | 4/1995 | Onodera et al. ............ 210/654 |
| 5,547,576 | 8/1996 | Onishi et al. ............ 210/500.37 |

FOREIGN PATENT DOCUMENTS

| | | |
|---|---|---|
| 0285357 A2 | 10/1988 | European Pat. Off. . |
| 0307373 A2 | 3/1989 | European Pat. Off. . |
| 0320184 A1 | 6/1989 | European Pat. Off. . |
| 0406512 A1 | 1/1991 | European Pat. Off. . |
| 2669535 | 5/1992 | France . |
| 2-36878 | 2/1990 | Japan . |
| 2-167232 | 6/1990 | Japan . |
| 3-123630 | 5/1991 | Japan . |
| 4-309502 | 3/1993 | Japan . |
| WO 89/01813 | 3/1989 | WIPO . |

*Primary Examiner*—John Kim
*Attorney, Agent, or Firm*—Burns, Doane, Swecker & Mathis, LLP

[57] ABSTRACT

A material for removing human immunodeficiency virus (HIV) and its related substances from blood, plasma, or other body fluids is provided. The material comprises a porous substrate on which sulfuric group substantially in the form of a salt is immobilized. A convenient removal of HIV and its related substances at a high efficiency is enabled by the use of the material.

10 Claims, No Drawings

MATERIAL FOR REMOVING HIV AND ITS RELATED SUBSTANCES

FIELD OF THE INVENTION

This invention relates to a material for removing human immunodeficiency virus (HIV) and the related substances from a body fluid. More illustratively, this invention relates to a membrane which is capable of selectively adsorbing the HIV and its related substances to enable removal of such substances from protein rich solutions such as blood, plasma, and solutions containing blood components.

BACKGROUND OF THE INVENTION

Many virus particles have an isoelectric point (pI) of from 3 to 6, and such viruses are negatively charged in neutral pH range. When such viruses are located in highly pure water, the viruses may be adsorbed onto an appropriate substrate by electrostatic interaction between the virus and the substrate.

Japanese Patent Application Laid-Open No. 3(1991)-123630 discloses a virus removing material comprising a substrate such as a porous membrane having polyvinylpyridinium structure thereon. This porous material, however, suffered from non-specific adsorption of proteins, and when the material was used for virus removal from fluids such as blood and plasma, which usually contain proteins at a high concentration, it failed to selectively adsorb the virus.

Another filter for removing virus from body fluids and other protein solutions is disclosed in Japanese Patent Application Laid-Open No. 2(1990)-167232. This filter comprises a regenerated cellulose membrane having a pore size smaller than the HIV particle, and the passage of the HIV particles upon filtration through the membrane is thereby inhibited. Such small pore size, however, also resulted in low filtration rate as well as frequent clogging. In addition, there has been reported that the pathogenicity of the HIV is found not only in the HIV particle, but also in the envelope proteins such as gp120 and gp160 (see, for example, *Microbiological Reviews*, March 1993, pages 183–289, "Pathogenesis of HIV infection".) The pore size of this filter is not small enough to capture the gp120.

Another virus removing material is disclosed in WO89/01813, that utilizes biological affinity for the removal of the virus from the blood or plasma. This material comprises a substrate having immobilized thereon a virus-binding site (receptor) of a cell, that is found on the surface of the cell. Production of such material, however, involves complicated steps of isolation of the receptor from the cell and its purification followed by immobilization of the purified receptor onto the substrate. Use of such receptor of biological origin also resulted in an increased cost and some risk of unstable performance and alteration in the quality after storage.

Japanese Patent Application 2(1990)-36878 (U.S. Pat. No. 5,041,079) discloses a material for removing HIV and its related substances comprising a solid substance with a weakly acidic or weakly alkaline surface at a pH of from 2.5 to 6.9 or from 7.4 to 10.5. This material may typically have —COOH or —SO$_3$H on its surface, and there is clearly stated that "substances whose surface pH is in the range 7.0 to 7.3 (e.g. nonpolar polypropylene, quartz, and cation-exchange resins of —SO$_3$Na type) are unable to absorb HIV and/or its related compounds" (col. 2, lines 29 to 33 in U.S. Pat. No. 5,041,079). Furthermore, it has been confirmed that the body fluid would undergo an alteration in its pH upon contact with such an HIV removing material, and use of such material is not necessarily favorable for blood and other body fluids since such alteration in the pH may result in the denaturing of the proteins.

SUMMARY OF THE INVENTION

In view of the situation as described above, an object of the present invention is to provide a material by which HIV and its related substances can be removed from protein rich solutions such as blood and plasma preparations at a high selectivity and by a convenient operation.

To attain such object, there is provided by the present invention a material for removing HIV and its related substances comprising a porous substrate having a plurality of pores wherein said pores have sulfuric group substantially in the form of a salt such as potassium or sodium salt on their surface.

Preferably, the intervening hydrophilic graft chain is a side chain grafted the porous substrate such as alkoxy alkyl acrylate or glycidyl acrylate.

The porous substrate is preferably a porous membrane comprising a hydrophobic polymer such as polypropylene, polyethylene or polyvinylidene fluoride having an average pore diameter of from 0.1 to 1 µm; and the porous membrane may preferably have a polysulfuric compound loaded on its pore surface.

The polysulfuric compound may be loaded on the porous membrane with an intervening hydrophilic graft chain having a low protein adsorptivity, such as those comprising an acrylamide polymer, a polyether polymer, or a polyalkoxyalkyacrylate polymer such as polymethoxyethylacrylate.

The polysulfuric compound may preferably be selected from dextran sulfate; cellulose sulfate; cardran sulfate; polymers and copolymers of sulfoethylacrylate, vinyl sulfate, and styrene sulfonic acid.

The material may preferably have 1×10$^{-4}$ mol/g or more of the sulfuric group on the porous membrane substrate, preferably the sulfuric group is a salt of potassium or sodium.

According to the present invention there is also provided a method for removing HIV and related substances from blood by adsorption simultaneously with the separation of the plasma from the blood. In this method, the blood is filtered through a porous membrane having an average pore diameter of from 0.1 to 1 µm wherein the pores have sulfuric group substantially in the form of a salt loaded on their surface.

According to the present invention there is also provided a method for removing HIV and related substances from blood or plasma by adsorption. In this method, the blood or plasma is contacted with a porous substrate wherein the pores have sulfuric group substantially in the form of a salt loaded on their surface.

DESCRIPTION OF THE INVENTION

In the present invention, the "material for removing human immunodeficiency virus (HIV) and its related substances" is a material that removes or inactivates the HIV and related substances, and preferably, a material that removes the HIV and its related substances from blood or other body fluids by adsorption onto the material.

The "HIV related substances" include glycoproteins constituting the HIV such as gp120 and 8P160, that are reported to be pathogenic, and complexes of such glycoproteins with a biological component.

The material for removing HIV and its related substances has on its surface sulfuric group substantially in the form of a salt, namely, in the form of potassium salt (—SO$_3$K), sodium salt (—SO$_3$Na), or the like in contrast to the sulfuric group of proton type (—SO$_3$H) as employed in Japanese Patent Application Laid-Open No.2(1990)-36878 (U.S. Pat. No. 5,041,079). As mentioned above, when a protein solution such as a body fluid is brought in contact with the material having the sulfuric group of proton type on its surface, the protein that became in contact with the sulfuric group would undergo an alteration in its pH by ion exchange reaction, and the HIV inactivation thus proceeds simultaneously with the adsorption and denaturing of other proteins. In contrast to such material, the material wherein the sulfuric group is in the form of a salt exhibits reduced non-specific protein adsorption as well as improved removal of the HIV and related substances including the gp120.

The material for removing HIV and its related substances may preferably have $1 \times 10^{-4}$ mol/g or more of the sulfuric group on its surface although the amount of the sulfuric group required may vary in accordance with the configuration of the material. When the amount of the sulfuric group is less than $1 \times 10^{-4}$ mol/g, the material would exhibit an insufficient removal of the HIV and gp120. The material may more preferably have $2 \times 10^{-4}$ mol/g or more of the sulfuric group preferably localized on its surface that becomes in contact with the liquid to be treated.

The characteristic feature of the material for removing HIV and its related substances of the present invention is its ability to selectively remove the HIV and its related substances from the liquid such as blood that contains a variety of proteins, and it is such feature that enables the material of the present invention to be used in treating the patient suffering from HIV infection such as AIDS (acquired immune deficiency syndrome) and ARC (AIDS related conditions). In the treatment of AIDS, it is important to prevent the virus from spreading, to reduce the load imposed by the virus, and to inhibit the virus replication. Removal of HIV, gp120 and the like from the body fluid of the patient suffering from HIV blood conditions should result in the reduction of the virus load and prevention of the virus spread, and hence, in the improvement of the QOL (quality of the life) of the patient and suppression of the disease progress.

The removal of the HIV and its related substances by the material of the present invention is represented by the reduction in the HIV infectious titer calculated in terms of median tissue culture infectious dose (TCID$_{50}$)/ml by the use of the material. For example, when a disk-shaped filter having a diameter of 25 mm is used by passing 2 ml of plasma having an infectious dose of from several tens to several hundreds TCID$_{50}$/ml (corresponding to the treatment of about 10 liters of plasma or about 20 liters or more of blood by a module having a membrane area of 0.5 m$^2$), the filter should exhibit an HIV removal of 85% or higher, and preferably, 90% or higher, and more preferably, 95% or higher.

In the present invention, loading of the sulfuric group on the material means chemical binding or immobilization of the sulfuric group on the material surface in a manner that the sulfuric group would not dissolve into water or blood. Such loading may be accomplished by various means, for example, by introducing a functional radical such as epoxy, amino, aldehyde, carboxyl, hydroxyl, or acid chloride group on the surface of the polymer material by such means as graft polymerization, coating, chemical modification, oxidization, and cross linking, and immobilizing the polysulfuric compound directly on the thus treated material by using or without using a coupling agent, or indirectly with an intervening spacer.

In a preferred method, a surface graft chain having a reactive functional radical may be introduced on the surface of the polymer material, and a polysulfuric compound may be immobilized on the reactive functional radical. In another method, the material surface is sulfated with sulfuric acid or sulfite to form a surface structure wherein a polysulfuric compound is loaded on the material surface. Preferably, such sulfation of the material surface is carried out after graft polymerizing a compound having epoxy group or hydroxyl group on the material surface.

The graft chain having a reactive functional radical may preferably comprise a monomer component such as glycidyl acrylate and glycidyl methacrylate having epoxy group therein, since the epoxy group may be changed to an amino group for reacting with a sulfuric group.

The polysulfuric compound are not limited to any particular type so long as it has a plurality of sulfuric group in its molecule. Exemplary polysulfuric compounds are sulfated polysaccharides such as dextran sulfate, cellulose sulfate, and cardran sulfate; and polymers and copolymers of a sulfonated monomer such as sulfoethylacrylate, vinyl sulfate, and styrene sulfonic acid. Preferably, the polysulfuric compound is immobilized on the material by forming a hydrophilic graft chain having a glass transition temperature (Tg) of up to 300K that exhibits a low protein adsorption comprising an acrylamide polymer, a polyether polymer, a polyalkoxyalkylacrylate polymer or the like on the material surface; introducing the above-described surface graft chain having a reactive functional radical; and immobilizing the polysulfuric compound on the reactive functional radical.

An Example of the methods for producing the material of this invention are shown schematically hereinafter.

The polyolefin membrane 1 such as polypropylene is irradiated with plasma to introduce radical points on the surface, and the surface is contacted with a alkoxy alkyl acrylate gas and/or a glycidyl acrylate gas to introduce graft polymerized side chains having active group such as epoxy group or hydroxyl group.

Optionally, the active groups may be changed the other active groups, then the active groups may be reacted with sulfuric groups, preferably in an aqueous solution.

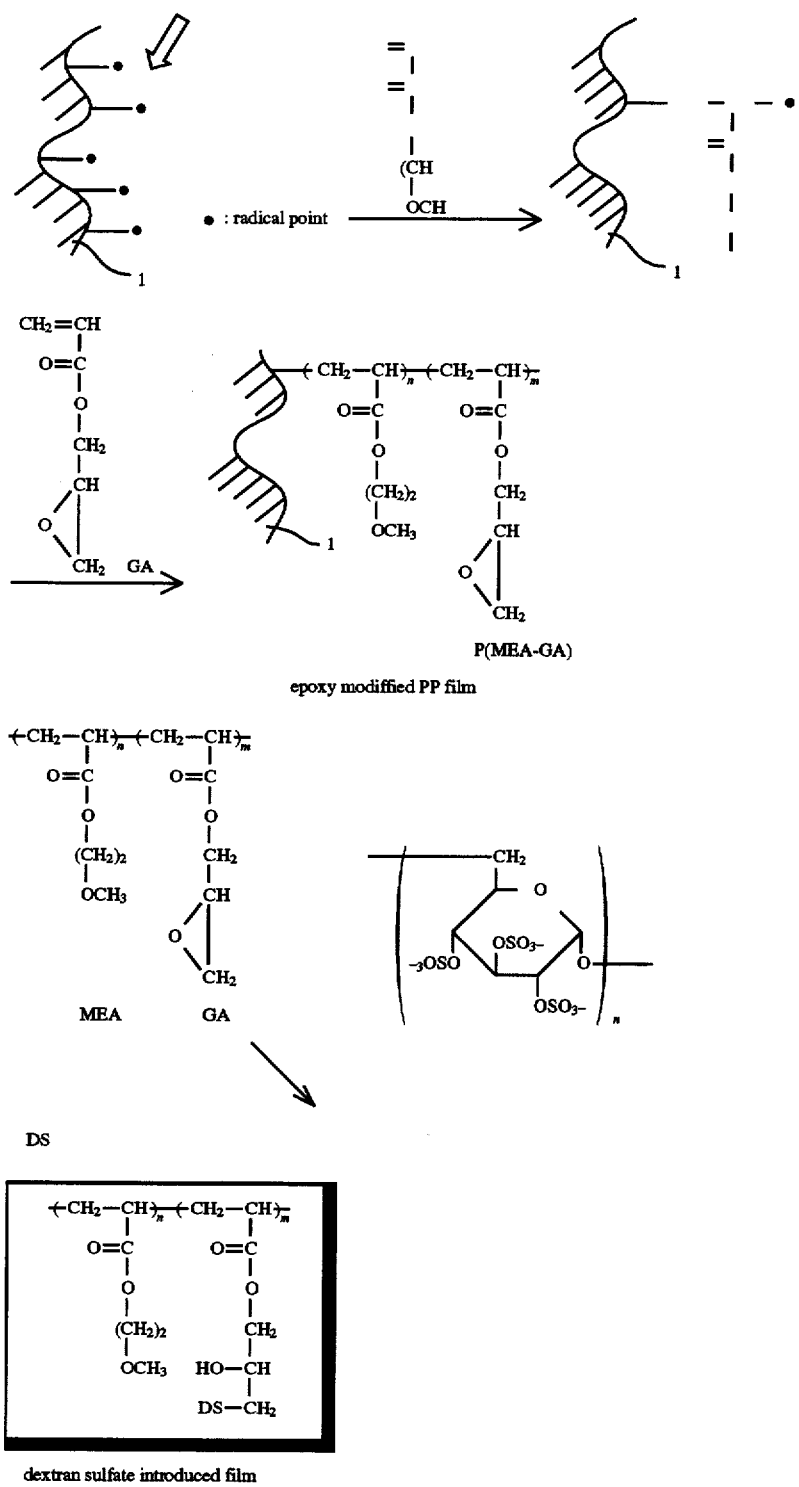

The material for removing HIV and its related substances of the present invention is not limited in its configuration and may have any desired configuration such as a fiber, a filter, or a tube. Preferably, the material is a filter having an average pore diameter of from 0.1 to 50 μm comprising a flat membrane, a hollow fiber, a woven fabric, or a nonwoven fabric.

When the material of the invention is used for filtering plasma or a culture medium, the filter may preferably have an average pore diameter of 0.1 to 10 μm. The pore diameter of as small as less than 0.1 μm will result in an insufficient filtration rate. The average pore diameter as used herein is the value determined by Perm-Porometer (manufactured by Porous Materials, Inc.) described in ASTM-F316, and this value satisfactorily reflects the actual pore diameter.

Preferably, the filter may also have a water transmission of at least 10 ml/min/m$^2$/mmHg, and more preferably, at least 100 ml/min/m$^2$/mmHg when measured at a pressure of 0.7 kg/cm$^2$ and at 25° C.±2° C., and then, the filter can be used at a relatively low filtration pressure.

When the material of the invention comprises a nonwoven fabric substrate, the nonwoven fabric substrate may comprise either a monofilament or a multifilament, but the filament should have an average diameter (an average of major diameter and minor diameter determined by observation with scanning electron microscope) of up to 100 µm and preferably, up to 50 µm. The membrane filter will then have a sufficient surface area, and hence, a sufficient adsorption site. It is also possible to use a profile filament, or alternatively, a porous filament. The filter material of the present invention may have a porosity (percentage of the pore volume) as determined by the following formula (A) of at least 20%, and preferably, at least 50%.

$$\text{Porosity (\%)} = \frac{\text{Volume of the pores}}{\text{Volume of}} \times 100 \quad (A)$$
(the pores and the filter material)

The material for removing HIV and related substances of the present invention may comprise any desired material including natural polymers such as cellulose and its derivatives; and synthetic polymers such as polyolefin, polyamide, polyimide, polyurethane, polyester, polysulfone, and polyacrylonitrile. Preferably, the material of the invention may comprise a material with a high dimensional stability that may experience little swelling upon contact with water. Exemplary such materials include hydrophobic polymers such as polypropylene and polyvinylidene fluoride. The material used in the present invention may preferably have its surface modified, polymerized or treated by hydrophylic materials to introduce sulfuric group and to prevent from adsorption of proteins.

As described above, the solution treated by the material of the present invention may include various proteins in addition to the HIV and its related substance. Exemplary solutions that may be treated by the material of the invention include body fluids such as blood, plasma, serum and urine and a liquid containing such a body fluid; and tissue or cell culture medium, supernatant thereof, and a liquid containing such a culture medium or supernatant.

The blood or blood containing solution treated by the material of the present invention may preferably be treated with removing blood cells.

The solution treated that may possibly contain HIV or its related substance is contacted with the material of the present invention to thereby reduce the HIV activity or the risk of HIV infection. The material may be contacted with the solution by batchwise immersion of the material in the solution; or by continuous passage of the solution through the material in the form of a column or a filter, the filtration through the filter-shaped material being the most preferred.

When the material for removing the HIV and its related substance may be in the form of a porous filter or a bead. Preferably the porous filter has an average pore diameter of from 0.1 to 1.0 µm, and has the sulfate group on its pore surface substantially in the form of a salt, it may be used as a horizontal filter in the filtration of blood to thereby accomplish plasma separation simultaneously with the removal by adsorption of the HIV and its related substances. Use of such filter also enables a convenient preparation of the HIV removing system.

The material and the method for removing HIV and its related substances of the present invention is further described by referring the Examples of the invention and Comparative Examples, which by no means limit the scope of the invention.

EXAMPLES

Examples 1 and 2 and Comparative Examples 1 and 2

A polypropylene (pp) membrane having an average pore diameter of 0.5 µm, a porosity of 58%, and a thickness of 80 µm was irradiated with argon plasma (100 W, 0.1 Torr, 15 sec.), and the membrane was contacted with 2-methoxyethyl acrylate (MEA) gas (1.0 Torr) for 3 minutes, and glycidyl acrylate (GA) gas (0.7 Torr) for 7 minutes to promote surface graft polymerization. The resulting hydrophilic porous membrane having epoxy group introduced on its surface was immersed in aqueous ammonia of high concentration at 40° C. for 48 hours to convert the epoxy group to amino group and produce an aminated hydrophilic porous membrane.

In the meanwhile, dextran sulfate (DS) (manufactured by Sigma; molecular weight, 5,000; degree of sulfation, 2.2) was oxidized with sodium periodate at a predetermined concentration (5% by weight) to produce aldehydated dextran sulfate.

The aminated hydrophilic porous membrane was reacted with the aldehydated dextran sulfate in water, and the resulting membrane was reduced with 10% by weight aqueous solution of NaBH$_4$ to strengthen the bond between the sulfate group and the membrane.

Sample membranes of Examples 1 and 2 wherein the sulfate group on the porous membrane is in the form of Na salt were prepared by neutralizing the membrane in sodium hydroxide and thoroughly rinsing the membrane with distilled water.

Sample membranes of Comparative Examples 1 and 2 wherein the sulfate group on the porous membrane is in the form of —SO$_3$H were prepared by treating the membrane with 0.1N dilute hydrochloric acid and rinsing the membrane with distilled water.

The amount of the sulfate group introduced on the membrane was determined by acid base titration (NaOH—HCl back titration).

The sample membrane was set on Swinrock Filter Holder (manufactured by Nuclepore; diameter, 25 mm), and 5 ml of HIV-containing human plasma (HIV infectious titer: 174 TCID$_{50}$/ml) was filtered through the membrane to measure HIV infectious titer and content of p24 before and after the filtration to thereby calculate the removal of the HIV and p24. The results are shown in Table 1. Removal of gp120, which is the glycoprotein found in HIV envelope, was measured by filtering 5 ml of 2% FCS-containing RPMI 1640 medium containing HIV through the membrane to measure the concentration of gp120 before and after the filtration, from which the gp120 removal was calculated. The results are also shown in Table 1.

The HIV-containing human plasma was prepared by cultivating HIV (HTLV-IIIB) persistently infected cell, Molt-4/HIV in 10% FCS-containing RPMI1640 and collecting the HIV solution by centrifugation, and adding human plasma to the HIV solution.

The HIV infectious titer was determined in terms of median tissue culture infectious dose (TCID$_{50}$)/ml by observing the cell morphology with naked eye and fluorescent antibody technique.

The p24 antigen was quantitated with RETRO-TEK p24 Antigen ELSA manufactured by Cellular Products, Inc.

TABLE 1

| | Sulfate group | | % removal | | |
|---|---|---|---|---|---|
| | Amount, mol/g | Type | HIV | gp120 | p24 |
| Example 1 | $7.2 \times 10^{-4}$ | —$SO_3Na$ | 99.2 | $\geq 95$ | $\geq 98$ |
| Example 2 | $3.7 \times 10^{-4}$ | —$SO_3Na$ | 97.2 | $\geq 95$ | $\geq 98$ |
| Comparable Example 1 | $7.2 \times 10^{-4}$ | —$SO_3H$ | 54.4 | 62 | 58 |
| Comparable Example 2 | $3.7 \times 10^{-4}$ | —$SO_3H$ | 58.2 | 55 | 52 |

Example 3 and Comparative Example 3

A polyvinylidene fluoride membrane having an average pore diameter of 0.4 μm, a porosity of 64%, and a thickness of 80 μm was irradiated with argon plasma (100 W, 0.1 Torr, 15 sec.), and the membrane was contacted with glycidyl acrylate gas (0.7 Torr) for 3 minutes to promote surface graft polymerization and produce a porous membrane having epoxy group introduced on its surface.

In the meanwhile, amino group was introduced into dextran sulfate (manufactured by Sigma; molecular weight, 5,000; degree of sulfation, 2.2) by means of 4-aminobutyldiethoxymethylsilane, and the aminated dextran sulfate was immobilized on the above-described porous membrane having epoxy group introduced thereon.

Sample membrane of Example 3 wherein the sulfate group is in the form of Na salt was prepared by neutralizing the membrane with sodium hydroxide and thoroughly rinsing the membrane with distilled water.

Sample membrane of Comparative Example 3 wherein the sulfate group is in the form of —$SO_3H$ were prepared by treating the membrane with 0.1N dilute hydrochloric acid and rinsing the membrane with distilled water.

The membranes were evaluated for their performance of HIV removal by repeating the procedure of Example 1.

The results are shown in Table 2.

TABLE 2

| | Sulfate group | | % removal of |
|---|---|---|---|
| | Amount, mol/g | Type | HIV |
| Example 3 | $5.3 \times 10^{-4}$ | —$SO_3Na$ | 98.2 |
| Comparable Example 3 | $5.3 \times 10^{-4}$ | —$SO_3H$ | 63.3 |

Examples 4 and 5 and Comparative Example 4

A polypropylene membrane having an average pore diameter of 0.4 μm, a porosity of 54%, and a thickness of 80 μm was irradiated with argon plasma (100 W, 0.1 Torr, 15 sec.), and the membrane was contacted with 2-methoxyethyl acrylate gas (1.0 Torr) for 3 minutes, and glycidyl acrylate gas (0.7 Torr) for 7 minutes to promote surface graft polymerization. The resulting hydrophilic porous membrane having epoxy group introduced on its surface was sulfated in a 20% sodium sulfite solution (40° C.) that had been acidified with sulfuric acid for 1, 12 and 24 hours to convert the epoxy group to sulfuric group.

Sample membranes of Examples 4 and 5 wherein the sulfate group on the porous membrane is in the form of Na salt were prepared by neutralizing the membrane in sodium hydroxide and thoroughly rinsing the membrane with distilled water.

Sample membrane of Comparative Example 4 wherein the sulfate group on the porous membrane is in the form of —$SO_3H$ was prepared by treating the membrane with 0.1N dilute hydrochloric acid and rinsing the membrane with distilled water.

The membranes were evaluated for its performance of HIV and gp120 removal by repeating the procedure of Example 1.

The results are shown in Table 3.

TABLE 3

| | Sulfate group | | % removal | |
|---|---|---|---|---|
| | Amount, mol/g | Type | HIV | gp120 |
| Example 4 | $7.5 \times 10^{-4}$ | —$SO_3Na$ | 99.5 | $\geq 95$ |
| Example 5 | $6.4 \times 10^{-4}$ | —$SO_3Na$ | 98.8 | $\geq 95$ |
| Comparable Example 4 | $4.6 \times 10^{-4}$ | —$SO_3H$ | 52.0 | 12 |

Comparative Examples 5 and 6

Various types of beads having sulfate group on their surface were compared for their performance of HIV removal. The beads were prepared to have capacity that would result in the amount of sulfate group nearly equivalent to the sulfated polypropylene membrane of Example 5 (see the total amount of $SO_3Na$ relative mole ratio in Table 4). The sulfated beads were contacted with the HIV in 3 ml 10% FCF-containing RPMI medium for 30 minutes by mixing with turning over the bottle. The performance of HIV removal was evaluated as in the case of Example 1.

The results are shown in Table 4.

TABLE 4

| | | Total amount of $SO_3Na$, relative mol ratio | % removal of HIV |
|---|---|---|---|
| Example 5 | Sulfated propylene membrane | $1.9 \times 10^{-5}$ | 99 |
| Comparable Example 5 | SP-Sepharose (manufactured by Pharmacia) | $2.1 \times 10^{-5}$ | 18 |
| Comparable Example 6 | IR120B (manufactured by Organo) | $1.9 \times 10^{-5}$ | 21 |

Comparative Examples 7 and 8

A polypropylene membrane having an average pore diameter of 0.4 μm, a porosity of 54%, and a thickness of 80 μm was irradiated with argon plasma (100 W, 0.1 Torr, 15 sec.), and the membrane was contacted with 2-methoxyethyl acrylate gas (1.0 Torr) for 3 minutes, and methacrylic acid gas (0.8 Torr) for 5 minutes to promote surface graft polymerization and produce a hydrophilic porous membrane having carboxyl group introduced on its surface.

Sample membrane of Comparative Examples 7 wherein the carboxyl group on the porous membrane is in the form of Na salt was prepared by neutralizing the membrane in sodium hydroxide and thoroughly rinsing the membrane with distilled water.

Sample membrane of Comparative Examples 8 wherein the carboxyl group on the porous membrane is in the form of —COOH were prepared by treating the membrane with 0.1N dilute hydrochloric acid and rinsing the membrane with distilled water.

The amount of the carboxyl group on the membrane was determined by acid base titration to be $6.3 \times 10^{-4}$ mol/g.

The sample membrane was set on Swinrock Filter Holder (manufactured by Nuclepore; diameter, 25 mm), and 5 ml of HIV-containing human plasma was filtered through the membrane to measure the performance of HIV removal by comparing the infectious titer before and after the filtration as in the case of Example 1.

The results are shown in Table 5.

TABLE 5

| | Carboxyl group | | % removal of |
|---|---|---|---|
| | Content, mol/g | Type | HIV |
| Comparable Example 7 | $6.3 \times 10^{-4}$ | —COONa | 10 |
| Comparable Example 8 | $6.3 \times 10^{-4}$ | —COOH | 10 |

The polycarboxylated membranes of both Na and H types exhibited the HIV removal of about 10%, which is significantly lower than the membrane of the present invention.

As described above, the material of the present invention is capable of removing the HIV and its related substances from blood and plasma. Therefore, the material of the invention may be used for adsorbing and removing the HIV and its related substances from the blood of the patient suffering from HIV infections (AIDS and ARC) in order to reduce the load of the patient and to thereby suppress further progress of the AIDS and improve the conditions. The material of the invention may also be used for reducing the HIV in blood and blood preparations to thereby reduce the risk of infection.

The material of the invention may be used in various conventional method and apparatus wherein a column or a membrane module is utilized. When the material of the present invention is used in health-related or medical products for the purpose of preventing, treating or diagnosing the disease, the material of the invention may be used alone or in combination with other materials by kneading, incorporating, or laminating the present material in other materials.

In addition to the use of the material of the present invention for the purpose of removing the HIV and its related substances from the protein-containing solution such as plasma, the material of the invention may be also used for various products that may become in contact with the blood, body fluids, or their droplets under the conditions where the risk of HIV infection is involved. Exemplary such products include medical and non-medical devices that are used for human and non-human organisms that are, or that may be infected by the HIV in medical fields and emergency treatments, as well as non-medical devices that are used by non-HIV-infected people for the purpose of preventing the HIV infection. The material of the present invention may also be used in products such as air filter for the purpose of providing an HIV-free environment.

We claim:

1. A membrane for removing substances absorbed thereon comprising a porous substrate having a plurality of pores wherein said pores have a polysulfuric compound loaded on their pore surface by an intervening hydrophilic graft chain having a reactive functional group which immobilizes the polysulfuric compound to the reactive functional group; wherein said sulfuric group of the sulfuric compound is substantially in the form of a salt; and further wherein said hydrophilic graft chain comprises at least one member selected from the group consisting of an acrylamide polymer, a polyether polymer, and a polyalkoxyalkylacrylate polymer.

2. The membrane for removing substances adsorbed thereon according to claim 1, wherein said porous substrate is a porous membrane comprising a hydrophobic polymer having an average pore diameter of from 0.1 to 1 μm.

3. The membrane for removing substances adsorbed thereon according to claim 1, wherein the hydrophilic graft chain has a low protein adsorptivity.

4. The membrane for removing substances adsorbed thereon according to claim 3, wherein said reactive functional group is selected from the group consisting of hydroxy and epoxy groups.

5. The membrane for removing substances adsorbed thereon according to claim 1, wherein said sulfuric group in the form of a salt is selected from the group consisting of potassium and sodium salts.

6. The membrane for removing substances adsorbed thereon according to claim 1, wherein said polysulfuric compound is selected from the group consisting of dextran sulfate, cellulose sulfate, cardran sulfate, polymers and copolymers of sulfoethylacrylate, vinyl sulfate, and styrene sulfonic acid.

7. The membrane for removing substances adsorbed thereon according to claim 1, wherein said porous substrate comprises at least one member selected from the group consisting of polypropylene and polyvinylidene fluoride.

8. The membrane for removing substances adsorbed thereon according to claim 1, wherein $1 \times 10^{-4}$ mol/g or more of said sulfuric group is loaded on the porous membrane substrate.

9. The membrane for removing substances adsorbed thereon according to claim 1, wherein said substance comprises HIV or a HIV related substance, wherein an HIV related substance is selected from the group consisting of HIV glycoproteins which constitute HIV and complexes comprising said HIV glycoproteins.

10. The membrane for removing substances adsorbed thereon according to claim 9, wherein said HIV glycoprotein is selected from the group consisting of gp120 and gp160.

* * * * *

UNITED STATES PATENT AND TRADEMARK OFFICE
CERTIFICATE OF CORRECTION

PATENT NO. : 5,667,684
DATED : September 16, 1997
INVENTOR(S) : Tadahiro MOTOMURA et al It is certified that error appears in the above-identified patent and that said Letters Patent is hereby corrected as shown below:

In Column 2, lines 31-32, delete "polyalkoxy-alkyacrylate" and insert -- polyalkoxy-alkylacrylate --.

In Column 5, lines 1-12, delete "

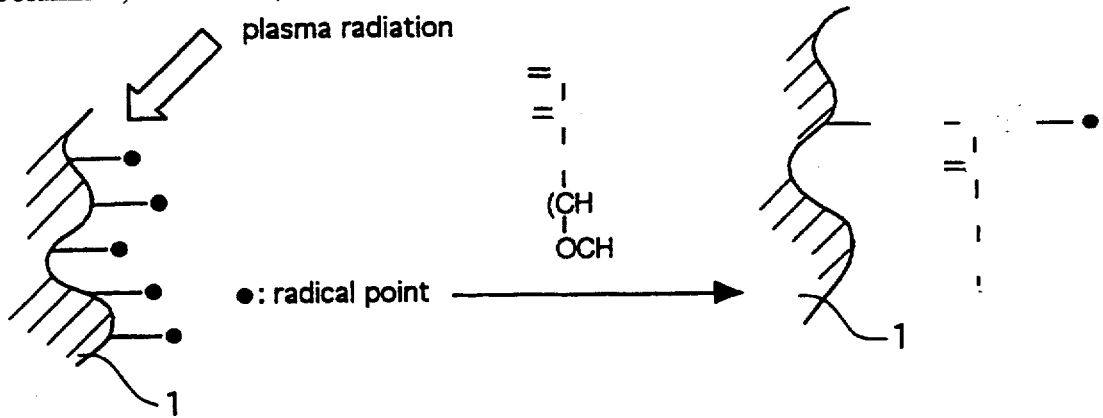

UNITED STATES PATENT AND TRADEMARK OFFICE
CERTIFICATE OF CORRECTION

PATENT NO. : 5,667,684

DATED : September 16, 1997

INVENTOR(S) : Tadahiro MOTOMURA et al

It is certified that error appears in the above-identified patent and that said Letters Patent is hereby corrected as shown below:

" and insert --

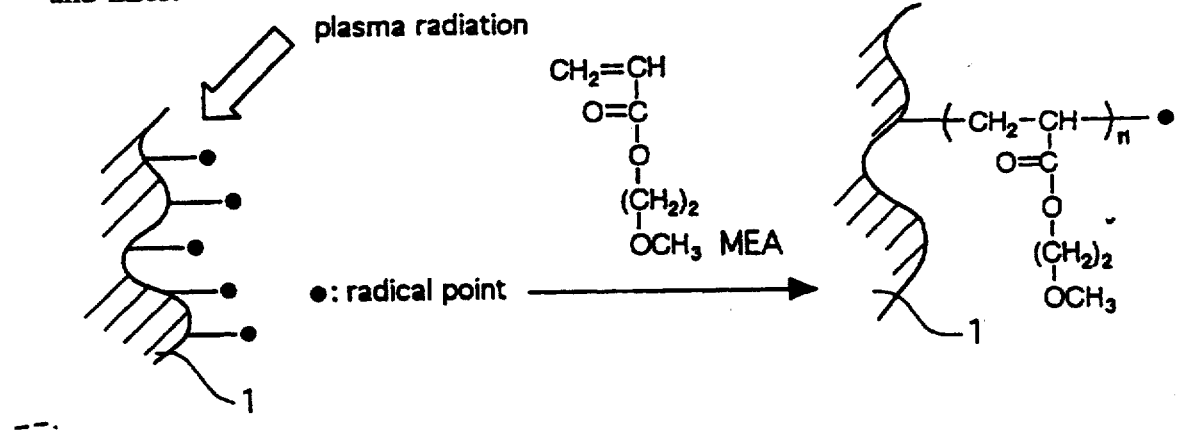

--.

Signed and Sealed this

Twenty-fourth Day of February, 1998

Attest:

BRUCE LEHMAN

Attesting Officer     Commissioner of Patents and Trademarks